(12) United States Patent
Schmidts et al.

(10) Patent No.: US 9,404,110 B2
(45) Date of Patent: Aug. 2, 2016

(54) DERMATOLOGICAL, PHARMACEUTICAL COMPOSITION SUITABLE FOR OLIGONUCLEOTIDES

(71) Applicant: STERNA BIOLOGICALS GMBH & CO. KG, Marburg (DE)

(72) Inventors: Thomas Schmidts, Giessen (DE); Holger Garn, Marburg (DE); Frank Runkel, Buseck (DE)

(73) Assignee: STERNA BIOLOGICALS GMBH & CO. KG, Marburg (DE)

( * ) Notice: Subject to any disclaimer, the term of this patent is extended or adjusted under 35 U.S.C. 154(b) by 0 days.

(21) Appl. No.: 14/965,371

(22) Filed: Dec. 10, 2015

(65) Prior Publication Data
US 2016/0115478 A1    Apr. 28, 2016

Related U.S. Application Data

(62) Division of application No. 13/578,013, filed as application No. PCT/EP2011/000648 on Feb. 11, 2011, now Pat. No. 9,249,413.

(30) Foreign Application Priority Data

Feb. 10, 2010 (DE) .................. 10 2010 007 562

(51) Int. Cl.
- *C07H 21/02* (2006.01)
- *C07H 21/04* (2006.01)
- *C12N 15/11* (2006.01)
- *C12N 15/113* (2010.01)

(52) U.S. Cl.
CPC .......... *C12N 15/113* (2013.01); *C12N 2310/11* (2013.01); *C12N 2310/127* (2013.01)

(58) Field of Classification Search
USPC ..................... 536/23.1, 24.33, 24.5
See application file for complete search history.

(56) References Cited

U.S. PATENT DOCUMENTS

| 6,472,521 | B1 | 10/2002 | Uhlmann et al. |
| 6,841,539 | B1 | 1/2005 | Mehta et al. |
| 7,291,721 | B2 | 11/2007 | Giles-Komar et al. |
| 7,612,182 | B2 | 11/2009 | Giles-Komar et al. |
| 7,833,786 | B2 | 11/2010 | Giles-Komar et al. |

(Continued)

FOREIGN PATENT DOCUMENTS

| DE | 10238298 A1 | 3/2004 |
| DE | 10254214 A1 | 6/2004 |

(Continued)

OTHER PUBLICATIONS

English-language translation of Official Action issued Jul. 7, 2015, by the Japanese Patent Office in Japanese counterpart priority application No. 2012552313.

(Continued)

*Primary Examiner* — Terra C Gibbs
(74) *Attorney, Agent, or Firm* — Marshall, Gerstein & Borun LLP

(57) ABSTRACT

The invention relates to a cosmetic and/or dermatological and/or pharmaceutical composition for the topical use and application of oligonucleotides, in particular antisense-oligonucleotides such as DNAzyme, siRNSs, asDNAs or ribozymes for use as an agent against inflammatory diseases by means of emulsions having a dispersed, internal, discontinous aqueous phase.

17 Claims, 6 Drawing Sheets

(56) References Cited

U.S. PATENT DOCUMENTS

| | | | |
|---|---|---|---|
| 7,955,597 | B2 | 6/2011 | Giles-Komar et al. |
| 7,964,579 | B2 | 6/2011 | Mehta et al. |
| 8,119,789 | B2 | 2/2012 | Sel et al. |
| 8,247,544 | B2 | 8/2012 | Sel et al. |
| 2005/0096287 | A1 | 5/2005 | Mehta et al. |
| 2005/0261222 | A1 | 11/2005 | Wolber et al. |
| 2006/0025363 | A1 | 2/2006 | Breitenbach et al. |
| 2006/0058256 | A1 | 3/2006 | Breitenbach et al. |
| 2008/0182808 | A1 | 7/2008 | Breitenbach et al. |
| 2009/0209623 | A1 | 8/2009 | Tomono et al. |
| 2010/0047192 | A1 | 2/2010 | Kurfurst et al. |
| 2011/0213014 | A1 | 9/2011 | Mehta et al. |
| 2013/0030038 | A1 | 1/2013 | Schmidts et al. |
| 2014/0141013 | A1 | 5/2014 | Giles-Komar et al. |

FOREIGN PATENT DOCUMENTS

| | | | |
|---|---|---|---|
| DE | 10346487 | A1 | 5/2005 |
| DE | 102004010547 | A1 | 11/2005 |
| DE | 102007020554 | A1 | 10/2008 |
| JP | 2002-515514 | A | 5/2002 |
| JP | 2007-507438 | A | 3/2007 |
| JP | 2009-506763 | A | 2/2009 |
| RU | 2 249 458 | C2 | 4/2005 |
| RU | 2 318 829 | C2 | 3/2008 |
| WO | WO-00/09673 | A1 | 2/2000 |
| WO | WO-2007/013411 | A1 | 2/2007 |

OTHER PUBLICATIONS

English-language translation of Official Action issued Jul. 7, 2015, by the Russian Patent Office in Russian counterpart priority application No. 2012552313.

German-language Communication pursuant to Article 94(3) EPC issued Mar. 16, 2015 by the European Patent Office for European Application No. 11 705 444.5-1455.

German-language Official Action issued Jan. 13, 2011, by the German Patent Office in connection with the German counterpart priority application No. 10 2010 007 562.0.

German-language Official Action issued Jun. 25, 2014, by the European Patent Office in connection with the German counterpart priority application No. 11 705 444.5.

International Search Report and Written Opinion for corresponding international application No. PCT/EP2011/000648, mailing date Feb. 6, 2012 (includes English translation of written opinion).

Japanese-language Official Action issued Dec. 24, 2014, by the Japanese Patent Office in connection with the Japanese counterpart priority application No. 10-2012-552313.

Russian-language Decision on Grant issued Jun. 26, 2015, by the Russian Patent Office in Russian counterpart priority application No. 2012137904.

Russian-language Official Action issued Feb. 2, 2015, by the Russian Patent Office in connection with the Russian counterpart priority application No. 2012137904/15(061502).

Uzagare et al., Application of ionic liquid 1-methoxyethyl-3-methyl imidazolium methanesulfonate in nucleoside chemistry, Green Chem., 5:370-2 (2003).

DERMATOLOGICAL, PHARMACEUTICAL COMPOSITION SUITABLE FOR OLIGONUCLEOTIDES

CROSS REFERENCE TO RELATED APPLICATIONS

This is a division of U.S. patent application Ser. No. 13/578,013 filed Aug. 9, 2012, which is the U.S. national phase of international application No. PCT/EP2011/000648, filed Feb. 11, 2011, which claims priority to German patent application No. 102010007562.0, filed Feb. 10, 2010, the disclosure of each of which is incorporated herein by reference.

REFERENCE TO SEQUENCE LISTING SUBMITTED ELECTRONICALLY

The content of the electronically submitted sequence listing in ASCII text file (Name: 46951a_SeqListing.TXT; Size: 35,775 bytes; and Date of Creation: Nov. 24, 2015) filed with the application is incorporated herein by reference in its entirety.

BACKGROUND OF THE INVENTION

Oligonucleotides are substances comprised of a few nucleotides (DNA or RNA building blocks) whose nucleotide sequence consists in general of approx. 10-100 nucleotide units. Oligonucleotides are known as primers, for example, which are used in the polymerase chain reaction (PCR). Antisense oligonucleotides are oligonucleotides which have a base sequence that is complimentary to a cellular, viral or synthetic RNA or DNA and which can bind them by Watson-Crick base pairing. Such molecules are often directed against functional mRNAs. Due to the specific binding to the mRNA, ultimately the formation of the respective protein which is encoded by this mRNA is prevented by blockade of translation.

Antisense molecules may belong to various molecular classes to which antisense DNA (asDNA), "small inhibitory" RNA (siRNA), ribozymes and DNAzymes also belong. The last two groups of molecules are characterized by an inherent catalytic activity, which may lead to direct cleavage of the bound target RNA among other things.

As an example, but not exclusively, the DNAzymes of DE 103 46 487.5 are disclosed as examples of DNAzymes for producing an agent against inflammatory diseases.

It is known in general that oligonucleotides are very sensitive to naturally occurring or recombinant nucleases. Nucleases are a group of ubiquitous enzymes which usually act as hydrolases at ester linkages and catalyze the degradation of oligonucleotides. Those skilled in the art are familiar with nucleases as DNAses or RNAses.

The sensitivity of oligonucleotides to nucleases is problematical in medical use of oligonucleotides in particular. In comparison with traditional drugs, oligonucleotides can be degraded rapidly by DNAses and RNAses, which leads to a short half-life and thus to a lower bioavailability in the target cells.

In order for oligonucleotides to also be usable medicinally (in particular therapeutically), they must be protected effectively from the nucleases. To do so, great efforts are being made throughout the world with various technical approaches to modify the structure of oligonucleotides by chemical modifications, for example, in order to increase their stability or to develop drug carrier systems, i.e., so-called drug delivery systems. These drug delivery systems include, for example, liposomes, nanoparticles, viral shell capsids and protamine oligonucleotide particles.

Many of these drug delivery systems have disadvantages; for example, they do not provide adequate protection from degradation by nucleases, they have poor uptake into the target cells and tissue or they retain toxic or problematical constituents, which have a negative effect on the efficacy of the oligonucleotides. For topical application in particular, there is not currently a suitable preparation with which oligonucleotides such as DNAzymes can be formulated and administered as agents against inflammatory diseases because the formulations are not adequately protected against bacteria, fungi and nucleases. Successful use of oligonucleotides in dermatology has so far been prevented by this lack of options for protection.

SUMMARY OF THE INVENTION

The present invention relates to a cosmetic and/or dermatological and/or pharmaceutical preparation for topical use and administration of oligonucleotides as agents against diseases. The invention relates in particular to emulsions having a dispersed, discontinuous, internal aqueous phase with which oligonucleotides are formulated and administered as agents for topical application against inflammatory diseases.

A stable effective formulation in the form of an emulsion with a dispersed, discontinuous, internal aqueous phase holding oligonucleotides in a stable emulsion, effectively protecting the oligonucleotides from enzymatic degradation by nuclease while permitting good uptake into the target cells and tissue has surprisingly been found.

BRIEF DESCRIPTION OF THE DRAWINGS

FIG. 1a shows WOW 146 (formulation with $MgSO_4$). FIG. 1b shows WOW 167 (formulation with NaCl) in comparison over a period of 150 days. The stability of the WOW 146 (formulation with $MgSO_4$) is higher than the stability of the WOW 167 (formulation with NaCl).

FIG. 2a shows the HPLC measurement of DNAzyme on the skin after 2 minutes. FIG. 2b shows the HPLC measurement of DNAzyme on the skin after 152 minutes. FIGS. 2a and 2b show that unprotected degradation of DNAzymes on the skin begins already after 2 minutes due to the DNAses present there and after 152 minutes the DNAzyme is almost completely degraded. This reaction takes place equally all oligonucleotides and is not limited to DNAzymes.

DETAILED DESCRIPTION OF THE INVENTION

1. Characterization of the Formulation

Figure 1A:
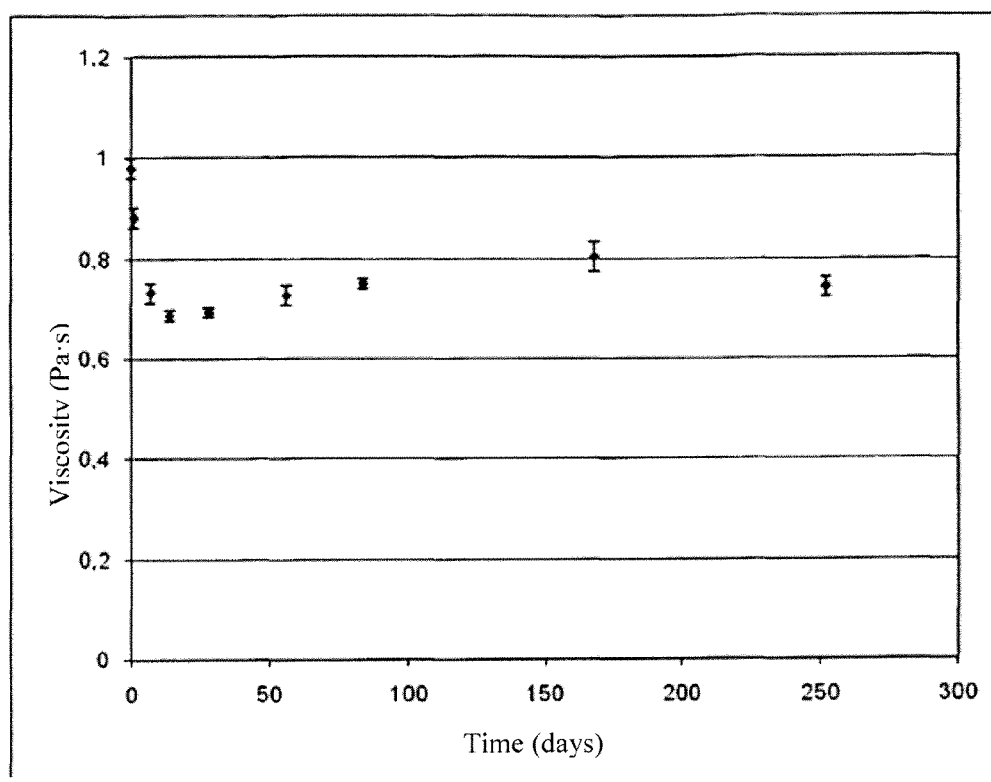
FIGS. 1a and 1b show the viscosity (Pa·s) of the DNAzyme-containing formulations.

The formulation according to the invention in the form of an emulsion with a dispersed, discontinuous, internal aqueous phase is formed by using the galenical form of the water-in-oil-in-water emulsion, the so-called WOW emulsion, and/or the water-in-oil emulsion, the so-called WO emulsion, with the addition of magnesium or sodium ions. It has surprisingly been found that adding magnesium or sodium ions to the formulation is very advantageous for the effect of the oligonucleotides, improving the stability of the oligonucleotides by protecting them from enzymatic degradation and thus permitting good absorption into the target cells, e.g., skin cells, lung and intestinal epithelial cells, mucosa, nasal epithelial cells and cells of the pharyngeal space.

SUBSTANCES OF THE FORMULATION ACCORDING TO THE INVENTION

The formulation according to the invention comprises at least one lipophilic emulsifier, at least one consistency agent, at least one occlusive component, at least one organic and/or inorganic additive, water and at least one oligonucleotide.

Alternatively, the formulation according to the invention additionally comprises at least one hydrophilic emulsifier and/or at least one amphiphilic component.

Alternatively, the formulation according to the invention additionally comprises at least one humectant factor.

Alternatively, the formulation according to the invention comprises at least one preservative.

Alternatively, the formulation according to the invention comprises at least one natural or synthetic oil or wax.

The at least one lipophilic emulsifier is selected from the group comprised of sorbitan fatty acid esters, glycerol derivatives (e.g., Spans, also glycerol stearate, glycerol dioleate, glycerol monooleate).

The at least one consistency agent is selected from the group comprised of fatty acid esters (e.g., cetyl palmitate, myristyl myristate), polyethylene glycols, cera alba, microcrystalline wax, lanolin and alcohols thereof, hydrogenated castor oil, carbomers (e.g., crosslinked acrylic acid polymers) or cellulose and its derivative.

The at least one occlusive component is selected from the group comprised of saturated hydrocarbons, e.g., paraffin or polysiloxanes such as silicone oils.

The at least one organic and/or inorganic additive is a salt or an ionic liquid whose cation component comprises Na, Mg, K, Li, Ca, Fe, Cu, Ag or a combination of these elements (e.g., a mixture of NaCl, $MgSO_4$) or a combination of these elements with organic cations (e.g., a mixture of $Mg(N(SO_2CF_3)_2)_2$, $Mg(OSO_2CF_3)_2$ in an ionic liquid, e.g., 1-ethyl-3-methylimidazolium chloride, 1-butyl-3-methylimidazolium tetrafluoroborate, 1-ethyl-3-methylimidazolium sulfate, 1-ethyl-3-methylimdazolium trifluoromethane sulfonate, 1-ethyl-3-methylimidazolium dicyanamide or 1-ethyl-1-methylpyrrolidinium bis(trifluoromethylsulfonyl)amide).

The at least one hydrophilic emulsifier is selected from the group comprised of polysorbates or ethoxylated polyethylene glycols (e.g., Tweens, steareths, laureths, cetearaths) or ethoxylated ether and/or esters.

The at least one amphiphilic component is selected from the group of phospholipids, preferably lecithin or one of its derivatives.

The at least one humectant factor is selected from the group of glycerol, polyols, osmolytes.

The at least one oil is selected from the group of esterified fatty acids (e.g., decyl oleate), waxes (e.g., jojoba wax) or partially esterified glycerides (e.g., medium-chain length triglycerides) or natural oils such as soy oil, peanut oil, avocado oil, olive oil, castor oil and nut oils or seed oils.

The at least one preservative is paraben, for example.

The at least one oligonucleotide is selected from the group comprised of primers, aptamers, antisense oligonucleotides, e.g., DNAzymes, siRNAs, asDNAs or ribozyme.

As an example but not exclusively, the DNAzymes of DE 103 46 487.5 are cited as the DNAzymes; they are directed against the mRNA of the proteins GATA-3 and T-bet and are disclosed for producing an agent against inflammatory diseases. For example, the following DNAzymes are used (each individually or in combination with the others):

Name of the DNAzyme against GATA-3 mRNA sequence:

hgd1
(SEQ ID NO: 1)
5'-TCGGTCAGAggctagctacaacgaTGCGTTGCT-3' hgd2
(SEQ ID NO: 2)
5'-GGCGTACGAggctagctacaacgaCTGCTCGGT-3' hgd3
(SEQ ID NO: 3)
5'-GGCGGCGTAggctagctacaacgaGACCTGCTC-3' hgd4
(SEQ ID NO: 4)
5'-CTCGGGTCAggctagctacaacgaCTGGGTAGC-3' hgd5
(SEQ ID NO: 5)
5'-TCCTCTGCAggctagctacaacgaCGGGGTCCT-3' hgd6
(SEQ ID NO: 6)
5'-ACTCTGCAAggctagctacaacgaTCTGCGAGC-3' hgd7
(SEQ ID NO: 7)
5'-GGGCGACGAggctagctacaacgaTCTGCAATT-3' hgd8
(SEQ ID NO: 8)
5'-AAGGGGCGAggctagctacaacgaGACTCTGCA-3' hgd9
(SEQ ID NO: 9)
5'-AAAACGGGAggctagctacaacgaCAGGTTGTA-3' hgd10
(SEQ ID NO: 10)
5'-AGAATAAAAggctagctacaacgaGGGACCAGG-3' hgd11
(SEQ ID NO: 11)
5'-ATGGCAGAAggctagctacaacgaAAAACGGGA-3' hgd12
(SEQ ID NO: 12)
5'-AACTGGGTAggctagctacaacgaGGCAGAATA-3' hgd13
(SEQ ID NO: 13)
5'-ATCCAAAAAggctagctacaacgaTGGGTATGG-3' hgd14
(SEQ ID NO: 14)
5'-AGGGGAAGAggctagctacaacgaAAAAATCCA-3' hgd15
(SEQ ID NO: 15)
5'-TTTTAAAAAggctagctacaacgaTATCTTGGA-3'

-continued hgd16
(SEQ ID NO: 16)
5'-GTGGGGGAggctagctacaacgaGGGAAGGCT-3' hgd17
(SEQ ID NO: 17)
5'-GTTGAATGAggctagctacaacgaTTGCTTTCG-3' hgd18
(SEQ ID NO: 18)
5'-GTCGTTGAggctagctacaacgaGATTTGCTT-3' hgd19
(SEQ ID NO: 19)
5'-GGCCCGGAggctagctacaacgaCCGCGCGCG-3' hgd20
(SEQ ID NO: 20)
5'-TCACCTCCAggctagctacaacgaGGCCTCGGC-3' hgd21
(SEQ ID NO: 21)
5'-CCGCCGTCAggctagctacaacgaCTCCATGGC-3' hgd22
(SEQ ID NO: 22)
5'-GGTGGCTCAggctagctacaacgaCCAGCGCGG-3' hgd23
(SEQ ID NO: 23)
5'-CGTTGAGCAggctagctacaacgaGGCGGGGTG-3' hgd24
(SEQ ID NO: 24)
5'-CCGCGTCCAggctagctacaacgaGTAGGAGTG-3' hgd25
(SEQ ID NO: 25)
5'-CAGCGGGTAggctagctacaacgaTGCGCCGCG-3' hgd26
(SEQ ID NO: 26)
5'-GCACATCCAggctagctacaacgaCTCCTCCGG-3' hgd27
(SEQ ID NO: 27)
5'-AAAAGCACAggctagctacaacgaCCACCTCCT-3' hgd28
(SEQ ID NO: 28)
5'-TAAAAAGCAggctagctacaacgaATCCACCTC-3' hgd29
(SEQ ID NO: 29)
5'-GACCGTCGAggctagctacaacgaGTTAAAAAG-3' hgd30
(SEQ ID NO: 30)
5'-TTGCCTTGAggctagctacaacgaCGTCGATGT-3' hgd31
(SEQ ID NO: 31)
5'-AGGGCGGGAggctagctacaacgaGTGGTTGCC-3' hgd32
(SEQ ID NO:32)
5'-TGGCCCTGAggctagctacaacgaCGAGTTTCC-3' hgd33
(SEQ ID NO: 33)
5'-ACCTCTGCAggctagctacaacgaCGTGGCCCT-3' hgd34
(SEQ ID NO: 34)
5'-CGGAGGGTAggctagctacaacgaCTCTGCACC-3' hgd35
(SEQ ID NO: 35)
5'-GGCGGCACAggctagctacaacgaCTGGCTCCC-3' hgd36
(SEQ ID NO: 36)
5'-CGGGCGGCAggctagctacaacgaACCTGGCTC-3' hgd37
(SEQ ID NO: 37)
5'-AGGGATCCAggctagctacaacgaGAAGCAGAG-3' hgd38
(SEQ ID NO: 38)
5'-GGGTAGGGAggctagctacaacgaCCATGAAGC-3' hgd39
(SEQ ID NO: 39)
5'-GGGCTGAGAggctagctacaacgaTCCAGGGGG-3' hgd40
(SEQ ID NO: 40)
5'-GTGGATGGAggctagctacaacgaGTCTTGGAG-3' hgd41
(SEQ ID NO: 41)
5'-CGTGGTGGAggctagctacaacgaGGACGTCTT-3' hgd42
(SEQ ID NO: 42)
5'-GGGGGTAGAggctagctacaacgaGGGAGAGGGG-3' hgd43
(SEQ ID NO: 43)
5'-GGAGGAGGAggctagctacaacgaGAGGCCGGG-3' hgd44
(SEQ ID NO: 44)
5'-GCCCCCCGAggctagctacaacgaAAGGAGGAG-3' hgd45
(SEQ ID NO: 45)
5'-CCGGGGAGAggctagctacaacgaGTCCTTCGG-3' hgd46
(SEQ ID NO: 46)
5'-GGACAGCGAggctagctacaacgaGGGTCCGGG-3' hgd47
(SEQ ID NO: 47)
5'-TGGGGTGGAggctagctacaacgaAGCGATGGG-3' hgd48
(SEQ ID NO: 48)
5'-CTTGAGGCAggctagctacaacgaTCTTTCTCG-3' hgd49
(SEQ ID NO: 49)
5'-CACCTGGTAggctagctacaacgaTTGAGGCAC-3' hgd50
(SEQ ID NO: 50)
5'-GCAGGGGCAggctagctacaacgaCTGGTACTT-3' hgd51
(SEQ ID NO: 51)
5'-CCAGCTTCAggctagctacaacgaGCTGTCGGG-3' hgd52
(SEQ ID NO: 52)
5'-GTGGGACGAggctagctacaacgaTCCAGCTTC-3' hgd53
(SEQ ID NO: 53)
5'-GGAGTGGGAggctagctacaacgaGACTCCAGC-3' hgd54
(SEQ ID NO: 54)
5'-ATGCTGCCAggctagctacaacgaGGGAGTGGG-3' hgd55
(SEQ ID NO: 55)
5'-GGGCGGTCAggctagctacaacgaGCTGCCACG-3'

-continued hgd56
(SEQ ID NO: 56)
5'-GAGGCTCCAggctagctacaacgaCCAGGGCGG-3' hgd57
(SEQ ID NO: 57)
5'-GTGGGTCGAggctagctacaacgaGAGGAGGCT-3' hgd58
(SEQ ID NO: 58)
5'-AGGTGGTGAggctagctacaacgaGGGGTGGTG-3' hgd59
(SEQ ID NO: 59)
5'-ACTCGGGCAggctagctacaacgaGTAGGGCGG-3' hgd60
(SEQ ID NO: 60)
5'-GGAGCTGTAggctagctacaacgaTCGGGCACG-3' hgd61
(SEQ ID NO: 61)
5'-GGACTTGCAggctagctacaacgaCCGAAGCCG-3' hgd62
(SEQ ID NO: 62)
5'-GGGCCTGGAggctagctacaacgaTTGCATCCG-3' hgd63
(SEQ ID NO: 63)
5'-TGTGCTGGAggctagctacaacgaCGGGCCTTG-3' hgd64
(SEQ ID NO: 64)
5'-GTTCACACAggctagctacaacgaTCCCTGCCT-3' hgd65
(SEQ ID NO: 65)
5'-CAGTTCACAggctagctacaacgaACTCCCTGC-3' hgd66
(SEQ ID NO: 66)
5'-CACAGTTCAggctagctacaacgaACACTCCCT-3' hgd67
(SEQ ID NO: 67)
5'-GTTGCCCCAggctagctacaacgaAGTTCACAC-3' hgd68
(SEQ ID NO: 68)
5'-TCGCCGCCAggctagctacaacgaAGTGGGGTC-3' hgd69
(SEQ ID NO: 69)
5'-CCCGTGCCAggctagctacaacgaCTCGCCGCC-3' hgd70
(SEQ ID NO: 70)
5'-GGCGTTGCAggctagctacaacgaAGGTAGTGT-3'

Name of the DNAzymes against T-bet mRNA sequence:

td1
(SEQ ID NO: 71)
5'-TGGCTTCTAggctagctacaacgaGCCCTCGTC-3' td2
(SEQ ID NO: 72)
5'-GGGCTCTGAggctagctacaacgaGCCTGGCTT-3' td3
(SEQ ID NO: 73)
5'-GGGACCCCAggctagctacaacgaCGGAGCCCG-3' td4
(SEQ ID NO: 74)
5'-GGTGGGGGAggctagctacaacgaCCCACCGGA-3'

-continued td5
(SEQ ID NO: 75)
5'-GGCGGGGGAggctagctacaacgaCCGAGGGCC-3' td6
(SEQ ID NO: 76)
5'-GGGCTGGGAggctagctacaacgaGGGCAGGGA-3' td7
(SEQ ID NO: 77)
5'-CGTCGAGGAggctagctacaacgaCCGCCCCTC-3' td8
(SEQ ID NO: 78)
5'-GGGCTGGCAggctagctacaacgaCTTCCCGTA-3' td9
(SEQ ID NO: 79)
5'-CGATGCCCAggctagctacaacgaCCGGGGCGG-3' td10
(SEQ ID NO: 80)
5'-GCTCCACGAggctagctacaacgaGCCCATCCG-3' td11
(SEQ ID NO: 81)
5'-CCGGCTCCAggctagctacaacgaGATGCCCAT-3' td12
(SEQ ID NO: 82)
5'-TCTCCGCAAggctagctacaacgaCCGGCTCCA-3' td13
(SEQ ID NO: 83)
5'-CCGTCAGCAggctagctacaacgaGTCTCCGCA-3' td14
(SEQ ID NO: 84)
5'-TCCCCGGCAggctagctacaacgaCGGCTCGGT-3' td15
(SEQ ID NO: 85)
5'-CCCCCGCGAggctagctacaacgaGCTCGTCCG-3' td16
(SEQ ID NO: 86)
5'-GTAGGGAGAggctagctacaacgaCCCAGGCTG-3' td17
(SEQ ID NO: 87)
5'-GGGCGGGCAggctagctacaacgaCAAGGCGCC-3' td18
(SEQ ID NO: 88)
5'-CGGGAAGGAggctagctacaacgaTCGCCCGCG-3' td19
(SEQ ID NO: 89)
5'-TAGTCCTCAggctagctacaacgaGCGGCCCCG-3' td20
(SEQ ID NO: 90)
5'-TCCCCGACAggctagctacaacgaCTCCAGTCC-3' td21
(SEQ ID NO: 91)
5'-TTTCCCCGAggctagctacaacgaACCTCCAGT-3' td22
(SEQ ID NO: 92)
5'-TGAGCGCGAggctagctacaacgaCCTCAGTTT-3' td23
(SEQ ID NO: 93)
5'-GGACCACAAggctagctacaacgaAGGTGGTTG-3' td24
(SEQ ID NO: 94)
5'-CTTGGACCAggctagctacaacgaAACAGGTGG-3' td25
(SEQ ID NO: 95)
5'-AAACTTGGAggctagctacaacgaCACAACAGG-3' td26
(SEQ ID NO: 96)
5'-CTGATTAAAggctagctacaacgaTTGGACCAC-3' td27
(SEQ ID NO: 97)
5'-TGGTGCTGAggctagctacaacgaTAAACTTGG-3' td28
(SEQ ID NO: 98)
5'-TGATGATCAggctagctacaacgaCTCTGTCTG-3' td29
(SEQ ID NO: 99)
5'-TGGTGATGAggctagctacaacgaCATCTCTGT-3' td30
(SEQ ID NO: 100)
5'-GCTTGGTGAggctagctacaacgaGATCATCTC-3' td31
(SEQ ID NO: 101)
5'-ATGGGAACAggctagctacaacgaCCGCCGTCC-3' td32
(SEQ ID NO: 102)
5'-GAATGGGAAggctagctacaacgaATCCGCCGT-3' td33
(SEQ ID NO: 103)
5'-TGACAGGAAggctagctacaacgaGGGAACATC-3' td34
(SEQ ID NO: 104)
5'-AGTAAATGAggctagctacaacgaAGGAATGGG-3' td35
(SEQ ID NO: 105)
5'-CACAGTAAAggctagctacaacgaGACAGGAAT-3' td36
(SEQ ID NO: 106)
5'-GCCCGGCCAggctagctacaacgaAGTAAATGA-3' td37
(SEQ ID NO: 107)
5'-CCACAAACAggctagctacaacgaCCTGTAGTG-3' td38
(SEQ ID NO: 108)
5'-GTCCACAAAggctagctacaacgaATCCTGTAG-3' td39
(SEQ ID NO: 109)
5'-CCACGTCCAggctagctacaacgaAAACATCCT-3' td40
(SEQ ID NO: 110)
5'-CCAAGACCAggctagctacaacgaGTCCACAAA-3' td41
(SEQ ID NO: 111)
5'-CCACCAAGAggctagctacaacgaCACGTCCAC-3' td42
(SEQ ID NO: 112)
5'-GCTGGTCCAggctagctacaacgaCAAGACCAC-3' td43
(SEQ ID NO: 113)
5'-GCTCTGGTAggctagctacaacgaCGCCAGTGG-3' td44
(SEQ ID NO: 114)
5'-CTGCACCCAggctagctacaacgaTTGCCGCTC-3' td45
(SEQ ID NO: 115)
5'-CACACTGCAggctagctacaacgaCCACTTGCC-3' td46
(SEQ ID NO: 116)
5'-CTTTCCACAggctagctacaacgaTGCACCCAC-3' td47
(SEQ ID NO: 117)
5'-GCCTTTCCAggctagctacaacgaACTGCACCC-3' td48
(SEQ ID NO: 118)
5'-TTCCTGGCAggctagctacaacgaGCTGCCCTC-3' td49
(SEQ ID NO: 119)
5'-GTGGACGTAggctagctacaacgaAGGCGGTTT-3' td50
(SEQ ID NO: 120)
5'-CCGGGTGGAggctagctacaacgaGTACAGGCG-3' td51
(SEQ ID NO: 121)
5'-CCTGGCGCAggctagctacaacgaCCAGTGCGC-3' td52
(SEQ ID NO: 122)
5'-CAAATGAAAggctagctacaacgaTTCCTGGCG-3' td53
(SEQ ID NO: 123)
5'-TTTCCCAAAggctagctacaacgaGAAACTTCC-3' td54
(SEQ ID NO: 124)
5'-ATTGTTGGAggctagctacaacgaGCCCCCTTG-3' td55
(SEQ ID NO: 125)
5'-TGGGTCACAggctagctacaacgaTGTTGGACG-3' td56
(SEQ ID NO: 126)
5'-TCTGGGTCAggctagctacaacgaATTGTTGGA-3' td57
(SEQ ID NO: 127)
5'-GCACAATCAggctagctacaacgaCTGGGTCAC-3' td58
(SEQ ID NO: 128)
5'-GGAGCACAAggctagctacaacgaCATCTGGGT-3' td59
(SEQ ID NO: 129)
5'-ACTGGAGCAggctagctacaacgaAATCATCTG-3' td60
(SEQ ID NO: 130)
5'-ATGGAGGGAggctagctacaacgaTGGAGCACA-3' td61
(SEQ ID NO: 131)
5'-TGGTACTTAggctagctacaacgaGGAGGGACT-3' td62
(SEQ ID NO: 132)
5'-GGGCTGGTAggctagctacaacgaTTATGGAGG-3' td63
(SEQ ID NO: 133)
5'-TCAACGATAggctagctacaacgaGCAGCCGGG-3' td64
(SEQ ID NO: 134)
5'-CCTCAACGAggctagctacaacgaATGCAGCCG-3'

-continued

```
td65
                                      (SEQ ID NO: 135)
5'-TCACCTCAAggctagctacaacgaGATATGCAG-3' td66
                                      (SEQ ID NO: 136)
5'-CGTCGTTCAggctagctacaacgaCTCAACGAT-3' td67
                                      (SEQ ID NO: 137)
5'-GTAAAGATAggctagctacaacgaGCGTGTTGG-3' td68
                                      (SEQ ID NO: 138)
5'-AAGTAAAGAggctagctacaacgaATGCGTGTT-3' td69
                                      (SEQ ID NO: 139)
5'-GGCAATGAAggctagctacaacgaTGGGTTTCT-3' td70
                                      (SEQ ID NO: 140)
5'-TCACGGCAAggctagctacaacgaGAACTGGGT-3' td71
                                      (SEQ ID NO: 141)
5'-AGGCAGTCAggctagctacaacgaGGCAATGAA-3' td72
                                      (SEQ ID NO: 142)
5'-ATCTCGGCAggctagctacaacgaTCTGGTAGG-3' td73
                                      (SEQ ID NO: 143)
5'-GCTGAGTAAggctagctacaacgaCTCGGCATT-3' td74
                                      (SEQ ID NO: 144)
5'-TATTATCAAggctagctacaacgaTTTCAGCTG-3' td75
                                      (SEQ ID NO: 145)
5'-GGGTTATTAggctagctacaacgaCAATTTTCA-3' td76
                                      (SEQ ID NO: 146)
5'-AAGGGGTTAggctagctacaacgaTATCAATTT-3' td77
                                      (SEQ ID NO: 147)
5'-CTCCCGGAAggctagctacaacgaCCTTTGGCA-3' td78
                                      (SEQ ID NO: 148)
5'-GTACATGGAggctagctacaacgaTCAAAGTTC-3'
```

Components of the WOW emulsion:

The WOW emulsion comprises at least one lipophilic emulsifier, at least one amphiphilic component, at least one consistency agent, at least one occlusive component, at least one organic or inorganic additive, at least one hydrophilic emulsifier.

In particular the WOW emulsion comprises at least one lipophilic emulsifier, where the lipophilic emulsifier is selected from the group comprised of sorbitan, fatty acid esters, glycerol derivatives (e.g., Spans).

At least one amphiphilic component, where this amphiphilic component is selected from the group comprised of phospholipids, preferably lecithin or one of its derivatives.

At least one consistency agent, where the consistency agent is selected from the group comprised of fatty acid esters (e.g., cetyl palmitate, myristyl myristate), polyethylene glycols, cera alba, microcrystalline wax, lanolin, hydrogenated castor oil, protegin W, protegin WX, carbomers (e.g., crosslinked acrylic acid polymers) or cellulose and its derivatives.

At least one occlusive component, where the occlusive component is a saturated hydrocarbon selected from the group comprised of paraffin or polysiloxanes such as silicone oils.

Alternative an oil selected from the group comprised of esterified fatty acids (e.g., decyl oleate), waxes (e.g., jojoba wax) or partially esterified glycerides (e.g., medium chain length triglycerides) or natural oils such as soy oil, peanut oil, avocado oil, olive oil, castor oil and nut or seed oils.

At least one organic and/or inorganic additive preferably a salt or an ionic liquid whose cation component comprises Na, Mg, K, Li, Ca, Fe, Cu, Ag or a combination of these elements.

At least one hydrophilic emulsifier where the hydrophilic emulsifier is selected from the group comprised of polysorbates, ethoxylated polyethylene glycols (e.g., Tweens, steareths, laureths, cetearths), ethoxylated ether, ethoxylated esters.

At least one oligonucleotide selected from the group of antisense oligonucleotides, e.g., DNAzymes, siRNAs, asDNAs or ribozymes or primers or aptamers.

Alternatively, the WOW emulsion additionally comprises at least one humectant factor where the humectant factor is selected from the group comprised of glycerol, polyols, osmolytes.

Alternatively, the WOW emulsion additionally comprises at least one preservative, e.g., paraben.

Ingredients of the WO emulsion:

The WO emulsion comprises at least one lipophilic emulsifier, at least one occlusive component, at least one consistency agent, at least one organic and/or inorganic additive, at least one hydrophilic emulsifier.

In particular the WO emulsion comprises at least one lipophilic emulsifier, where the lipophilic emulsifier is selected from the group comprised of sorbitan, fatty acid esters, glycerol derivatives (e.g., glycerol stearate, glycerol dioleates, glycerol monooleates).

At least one occlusive component wherein the occlusive component is a saturated hydrocarbon selected from the group comprised of paraffin or polysiloxanes such as silicone oils Alternatively, an oil selected from the group comprised of esterified fatty acids (e.g., decyl oleate), waxes (e.g., jojoba wax) or partially esterified glycerides (e.g., medium chain-length triglycerides) or natural oils such as soy oil, peanut oil, avocado oil, olive oil, castor oil as well as nut or seed oils.

At least one consistency agent, where the consistency agent is selected from the group comprised of fatty acid esters (e.g., cetyl palmitate, myristyl myristate), polyethylene glycols, cera alba, microcrystalline wax, lanolin or alcohols thereof, hydrogenated castor oil, protegin W, protegin WX, carbomers (e.g., crosslinked acrylic acid polymers) or cellulose and derivatives thereof.

At least one organic and/or inorganic additive, preferably a salt or an ionic liquid whose cationic component comprises Na, Mg, K, Li, Ca, Fe, Cu, Ag or a combination of these elements.

Alternatively, the WO emulsion additionally contains at least one humectant factor wherein the humectant factor is selected from the group comprised of glycerol, polyols, osmolytes.

At least one oligonucleotide selected from the group of comprised of antisense oligonucleotides, e.g., DNAzymes, siRNAs, asDNAs or ribozymes or primers or aptamers.

Alternatively, the WO emulsion additionally comprises at least one preservative, e.g., paraben.

Preparation of the Emulsions

The pharmaceutical composition according to the invention for topical application, comprising at least one lipophilic emulsifier, at least one consistency agent, at least one occlusive component, at least one organic and/or inorganic additive and at least oligonucleotide is added by methods with which those skilled in the art are familiar.

The pharmaceutical composition according to the invention for topical application, comprising at least one lipophilic emulsifier, at least one consistency agent, at least one occlusive component, at least one organic and/or inorganic additive and at least one oligonucleotide is more or less fluid, is a shampoo, a solution, a lotion, a cream, ointment, milk, paste or foam. Alternatively, it is an aerosol and is administered via the lungs.

The pharmaceutical composition according to the invention for topical application, comprising at least one lipophilic emulsifier, at least one consistency agent, at least one occlusive component, at least one organic and/or inorganic additive and at least one oligonucleotide is more or less fluid, is used in particular in infants especially in human infants.

2. Use of an Agent for Treatment and Prevention of Diseases

The formulation according to the invention in the form of an emulsion having a dispersed internal continuous aqueous phase is suitable in particular for protecting the oligonucleotides through the addition of magnesium or sodium ions because it stabilizes the oligonucleotides and protects them from enzymatic degradation enabling good absorption into the target cells. Therefore the formulation according to the invention is suitable as a cosmetic and/or dermatologic and/or pharmaceutical preparation for topical application and administration. Due to the use of oligonucleotides, which are known to be effective against inflammatory diseases, for example, the DNAzymes of DE 103 46 487.5, the formulation according to the invention is therefore suitable for production of an agent for treatment and prevention of inflammatory diseases which is used for topical application.

The formulation according to the invention has good absorption of the oligonucleotides, e.g., the DNAzyme, in particular the DNAzyme of DE 103 46 487.5 into target cells in topical application, e.g., skin cells, lung cells and intestinal epithelial cells, mucosa, nasal epithelial cells and cells of the pharyngeal area.

EXAMPLES

Example 1

Exemplary Embodiment of WOW Emulsion

The DNAzyme-containing water-in-oil-in-water emulsions (WOW emulsions) according to the invention preferably include the following ingredients:

| WOW | (%) (range) |
|---|---|
| Lipophilic emulsifier | 0.5-20 |
| preferably sorbitan fatty acid ester, glycerol derivatives (e.g., Spans) | |
| Amphiphilic component | 0.05-5 |
| phospholipids preferably lecithin or one of its derivatives, | |
| Consistency agents, such as | 0.1-5 |
| fatty acid esters (e.g., cetyl palmitate, myristyl myristate), polyethylene glycols, cera alba, microcrystalline wax, lanolin, hydrogenated castor oil, carbomers (e.g., crosslinked acrylic acid polymers), protegin W, protegin WX or cellulose and its derivatives | |
| Occlusive component based on saturated hydrocarbons such as | 1-25 |
| paraffin or polysiloxanes such as silicone oils | |
| Alternatively, an oil selected from the group of esterified fatty acids (e.g., decyl oleate), waxes (e.g., jojoba wax) or partially esterified glycerides (e.g., medium chain length triglycerides) or natural oils such as soy oil, peanut oil, avocado oil, olive oil, castor oil and nut or seed oils | 1-25 |
| Organic and/or inorganic additives, e.g., a salt or ionic liquid whose cationic component comprises Na, Mg, K, Li, Ca, Fe, Cu, Ag or a combination of these elements | 0.01-2 |
| Oligonucleotide, e.g., one of the DNAzymes of DE 103 46 487.5 | 0.01-5 |
| Water | as needed |
| Hydrophilic emulsifier such as polysorbates or ethoxylated polyethylene glycols (e.g., Tweens, steareths, laureths, ceteareths) or ethoxylated ethers and/or esters | 1-8 |
| Humectant factors (e.g., glycerol, polyols, osmolytes) | 0.1-10 |
| Preservatives such as parabens | as needed |

3.1.1. Selected Exemplary Embodiments (WOW 167)

| WOW 167 | (% w/w) |
|---|---|
| Sorbitan monooleate | 4 |
| Lecithin | 0.2 |
| Paraffin | 15.8 |
| NaCl | 0.074 |
| DNAzyme hdg 40 | 0.4 |
| Water | to a total of 100 |
| Steareth 20 | 1 |
| Water + paraben | 59 |

3.1.2. Selected Exemplary Embodiments (WOW 146)

| WOW 146 | (% w/w) |
|---|---|
| Sorbitan monooleate | 4 |
| Lecithin | 0.2 |

-continued

| WOW 146 | (% w/w) |
|---|---|
| Paraffin | 15.8 |
| MgSO$_4$ × 7H$_2$O | 0.308 |
| DNAzyme hdg 40 | 0.4 |
| Water | to a total of 100 |
| Water + paraben, preserved Water (external phase) | 59 |

Example 2

Exemplary Embodiment of a WO Emulsion

The water-in-oils emulsions according to the invention containing DNAzyme (WO emulsions) comprise the following ingredients:

| WOW | (%) Range |
|---|---|
| A lipophilic emulsifier or a mixture of same such as sorbitan fatty acid esters or glycerol derivatives (glycerol stearates, glycerol dioleates, glycerol monooleates) | 1-15 |
| Occlusive component based on saturated hydrocarbons such as paraffin or polysiloxanes such as silicone oils | 10-70 |
| Alternatively, an oil selected from the group of esterified fatty acids (e.g., decyl oleate), waxes (e.g., jojoba wax) or partially esterified glycerides (e.g., medium chain length triglycerides) or natural oils such as soy oil, peanut oil, avocado oil, olive oil, castor oil as well as nut or seed oils | 10-70 |
| Consistency agents such as fatty acid esters (e.g., cetyl palmitate, myristyl myristate), polyethylene glycols, cera alba, microcrystalline wax, lanolin, hydrogenated castor oil, protegin W, protegin WX, carbomers (e.g., crosslinked acrylic acid polymers), or cellulose and its derivatives | 0.5-10 |
| Lanolin or its alcohols | 1-8 |
| Preservatives (e.g., parabens) | as needed |
| Organic and/or inorganic additives, e.g., a salt or ionic liquid whose cation component comprises Na, Mg, K, Li, Ca, Fe, Cu, Ag or a combination of these elements | 0.01-2 |
| Oligonucleotide, e.g., one of the DNAzymes of DE 103 46 487.5 | 0.01-5 |
| Humectant factors (e.g., glycerol, polyols, osmolytes) | 0.1-10 |

| WO 126 | (% w/w) |
|---|---|
| Glycerol stearate | 1 |
| Glycerol monooleate (Imwitor 946) | 2 |
| Glycerol dioleate (Crossential GDO) | 2 |
| Paraffin | 38 |
| Cetyl palmitate | 2 |
| Lanolin | 3 |
| Hydrogenated castor oil | 2 |
| Preserved water + parabens | to a total of 100 |
| NaCl | 0.5 |
| DNAzyme hdg 40 | 0.4 |
| Glycerol | 3 |

| WO 162 | (% w/w) |
|---|---|
| Glycerol stearate | 1 |
| Glycerol monooleate (Imwitor 946) | 2 |
| Glycerol dioleate (Crossential GDO) | 2 |
| Paraffin | 38 |
| Cetyl palmitate | 2 |
| Lanolin | 3 |
| Water + paraben, preserved Water | to a total of 100 |
| MgSO$_4$ × 7H$_2$O | 1 |
| DNAzyme hdg 40 | 0.4 |
| Glycerol | 3 |

The oligonucleotide used is preferably any of the DNAzymes hgd 1-70 and td 1-78 disclosed in DE 103 46 487.5, preferably hgd 40 as a DNAzyme directed against GATA-3 at td 69 and/or td 70 as DNAzymes directed against T-bet.

Example 3

Stability Measurements on the Formulations

Figure 1B:
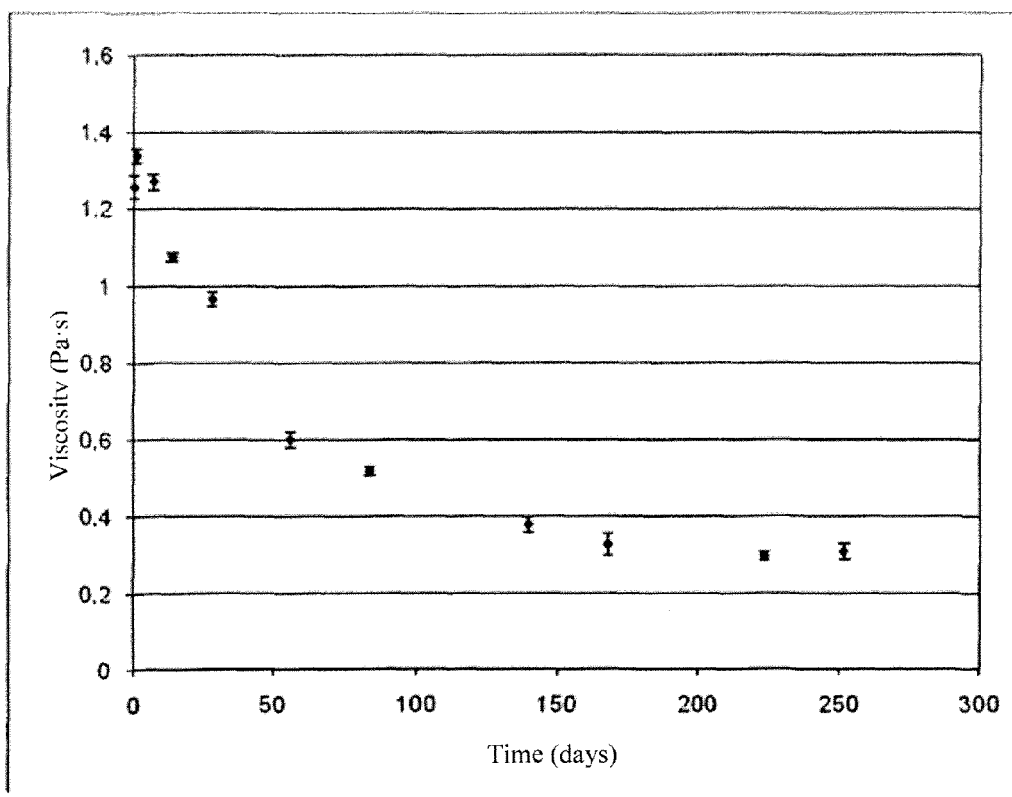

The formulations WOW 167 and WOW 146 containing DNAzyme according to the invention differ in the added electrolytes in the internal aqueous phase, which is represented graphically in FIG. 1. Solutions of 0.13M are preferably used here to prepare WOW 167 and WOW 146, because formulations with higher concentrations of electrolytes reduce the stability of the formulations. Stability is measured by comparison and over a period of 150 days.

Immediately after preparing the formulation, the viscosity of the WOW 167 (formulation with NaCl) is somewhat higher at 1.4 Pa·s than the viscosity of WOW 146 (formulation with MgSO$_4$) at 1 Pa·s. The viscosity of the WOW 146 formulation (formulation with MgSO$_4$) drops slightly to 0.75 Pa·s within the first 5 days, then remains largely unchanged at 0.75 Pa·s. The viscosity of the WOW 167 (formulation with NaCl) drops to 0.6 Pa·s by day 50 and then drops further to 0.4 Pa·s.

WOW 146 (formulation with MgSO$_4$) is thus much more stable than the WOW 167 (formulation with NaCl). It should be pointed out that the slight decline in viscosities does not have a negative effect on the stability or the protective action, and the emulsions do not exhibit any phase inversion or separation and are stable.

The measured droplet size is in the range of 10-20 μm.

The DNAzyme-containing formulations WO 162 and WO 126 according to the invention also differ in the electrolytes added to the internal water phase. The stability is measured by comparison and over a period of 150 days, where the viscosity remains unchanged for 150 days at approx. 4 Pa·s in the case of WO 126 and 4.2 for WO 162.

The droplet size here is in the range of 0.5-2.5 µm.

Example 4

Stability with Respect to Degradation by Nucleases Such as DNAses

The DNAzyme-containing WOW 167 and WOW 146 formulations according to the invention contain the DNAzymes of DE 103 46 487.5, namely DNAzymes hgd 1 to hgd 70 against GATA-3 and DNAzymes td 1 to td 78 against T-bet and protect them from degradation due to nucleases, in particular DNAses. It is important to protect the DNAzymes from degradation due to the DNAse, so that they can manifest their therapeutic efficacy.

A commercially available DNAse I with an activity of 105 U is used experimentally to measure the stability of the DNAzyme-containing formulations according to the invention with respect to DNAse and this was added to the WOW 167 and WOW 146 formulations. In addition, the degradation by a dermal lysate is used as a positive control. The degradation of the DNAzymes is determined by HPLC.

The measurement is performed using the following method:

Degradation of DNAzymes by DNAse from the skin

1) Method

Skin: approx. 50 mg

Solution: 1 mL DNAzyme standard (0.1625 mg/mL)+3 mL RO water (water from reverse osmosis)

Method: Skin pulverized using a scalpel and mixed with solution and shaken lightly, then filtered and degraded by HPLC after 2 min, 52 min, 102 min and 152 min.

Figure 2A:
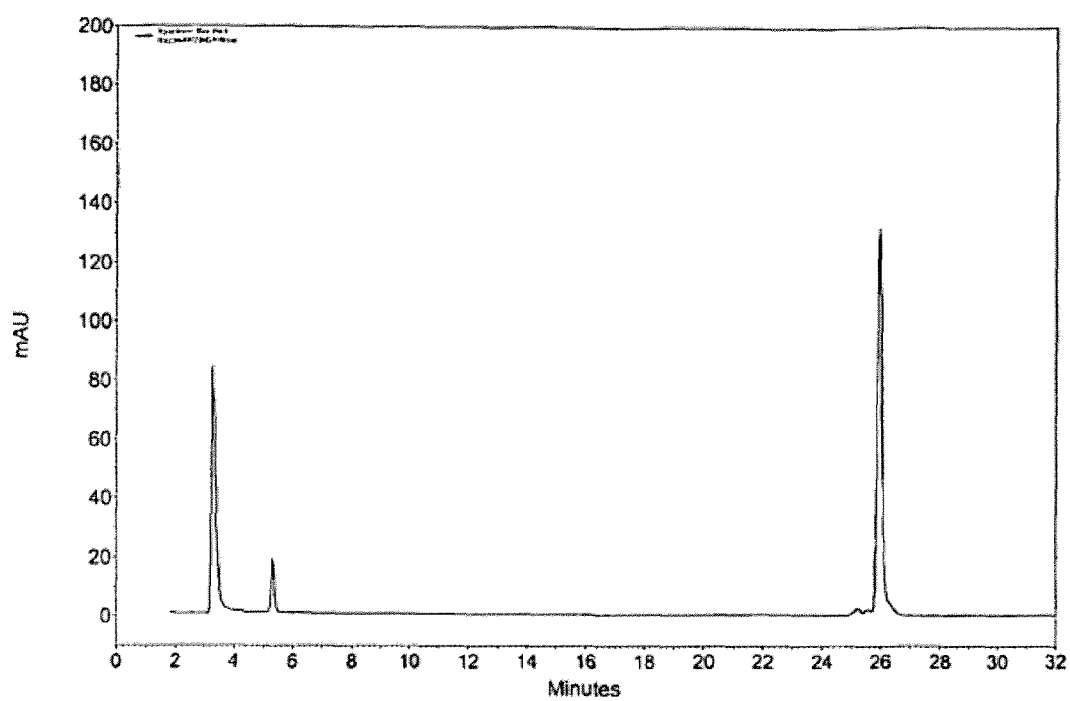
FIGS. 2a and 2b show the degradation of DNAzyme by DNAse from the skin, measured with HPLC.
Figure 2B:
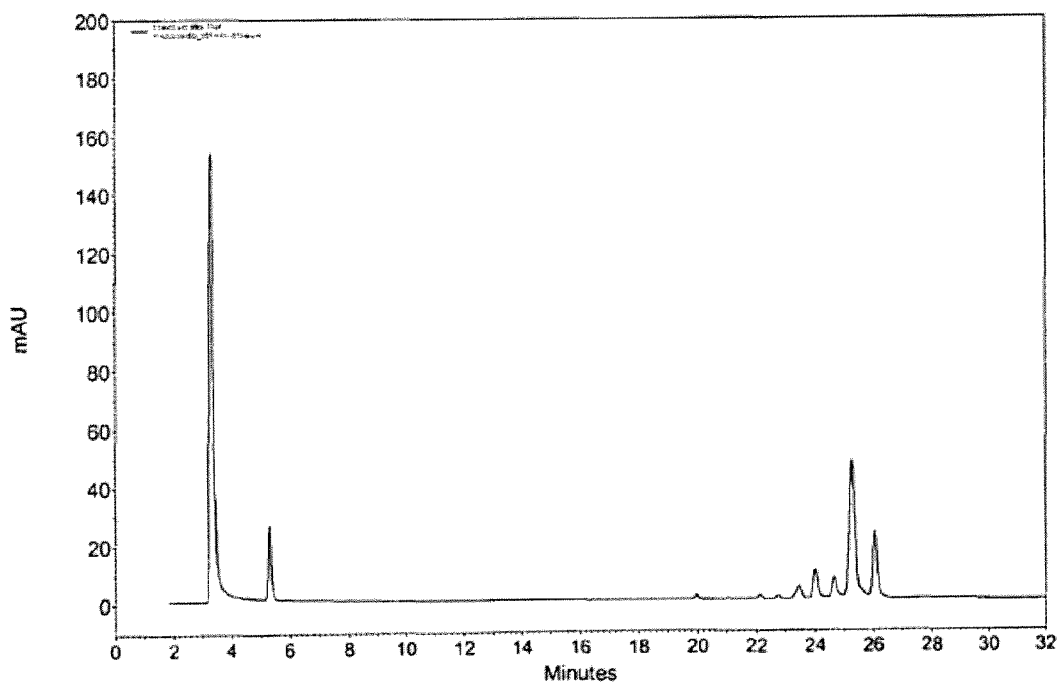

FIGS. 2a and 2b show that the DNAses naturally occurring in skin begin to degrade the DNAzyme after only 2 minutes; after 152 minutes almost the entire amount of DNAzyme is degraded.

Example 5

Protecting the DNAzymes from Degradation by DNAse Using the Formulations WOW 146, WOW 167, WO 126, WO 162 According to the Invention Galenical formulation 20 mg Solution: DNAse I with an activity of 105 U in Tris buffer+ 10 mM $MgSO_4$ Method: 20 mg of the respective formulation is mixed with 1 mL of a DNAse I solution. After an incubation time of 1 min, the mixture is agitated lightly at a temperature of 99° C. for 10 minutes in a thermomixer to stop the activity of the DNAse. To break the emulsion, the batch is incubated in an ultrasonic bath at 50° C. for 10 minutes. Then the batch is filtered through a 0.45 µm syringe filter and HPLC analysis is performed.

Figure 3:
FIG. 3 shows the protection of the formulations containing DNAzyme with respect to degradation by DNAse. This shows the WOW 146 formulation containing DNAzyme, which exhibit 90% protection of the DNAzymes, whereas the WOW 167 formulation containing DNAzyme exhibits only 60% protection. A standard solution (0.4% DNAzyme in PBS buffer) containing DNAzyme is used as the control.

FIG. 3 shows that the WOW 146 formulation offers approx. 61% protection of the DNAzymes from DNAse degradation, whereas 51% protection is achieved with the WOW 167 formulation. A standard solution containing DNAzyme (0.4% DNAzyme hgd 40 in PBS buffer (PBS=phosphate buffered saline solution ~137 mM NaCl, 2.7 mM KCl, 12 mM $Na_2HPO_4$ and $KH_2PO_4$, pH=7.4)) was used as the control, but no active ingredient could be recovered here. The WOW 167 formulation thus provides better protection on the whole. A comparable OW galenical formulation (microemulsion: preserved water, oil components, glycerol, hydrophilic emulsifier, magnesium sulfate) with the same amount of DNAzyme also failed to show any protection and 100% of the DNAzymes was degraded.

Example 6

Stability in Comparison with Oil-in-Water Formulations (OW Formulations)

For detecting the stability of the active ingredient in the galenical formulations, the recovery of 0.4% of the DNAzyme hgd 40 active ingredient in WO 162, WOW 146 was analyzed by HPLC after one month, using as the reference a comparable OW galenical formulation (microemulsion: preserved water, oil component, glycerol, hydrophilic emulsifier, magnesium sulfate).

The recovery of DNAzyme hgd 40 in comparison with the starting value of 100% after one month was 35.98±0.16% in the OW comparative galenical formulation. The recovery after one month in the WO 162 formulation was 95.66±2.77%. The recovery after one month in the WOW formulation was 103.15±2.29%.

Example 7

Detecting the Efficacy of GATA-3 DNAzyme Formulations in the Animal Model

The efficacy of the pharmaceutical composition according to the invention for topical application comprising at least one lipophilic emulsifier, at least consistency agent, at least one occlusive component, at least one organic and/or inorganic additive and at least one oligonucleotide as the agent for treatment of inflammatory skin diseases is illustrated on the example of GATA-3 DNAzyme-containing formulations in an animal model.

Figure 4:
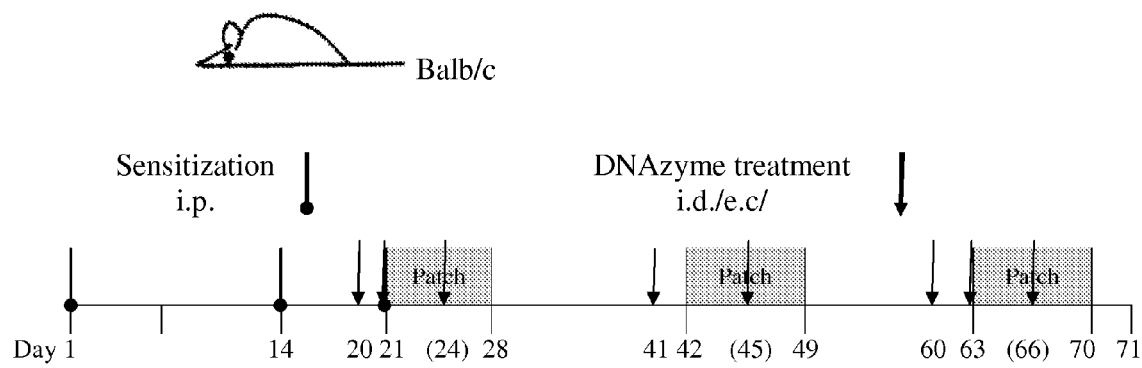
FIG. 4 shows the experimental setup of an animal model in which an inflammatory skin reaction is induced experimentally and the efficacy of agents for treatment of these diseases is tested.

To do so, a mouse model is used (see FIG. 4) in which a specific inflammation reaction in the skin of the mouse is induced by allergic sensitization using a model allergen such as ovalbumin UOVA) and subsequent repeated cutaneous administration by skin patches.

For sensitization, 10 µg OVA and 10 µg $AL(OH)_3$ in 100 µl PBS was administered intraperitoneally. For the patch test method, 100 µg OVA and 10 µg $AL(OH)_3$ was applied epicutaneously. For DNAzyme treatment, three formulations of 200 µg DNAzyme in 50 µl PBS were administered intradermally and/or epicutaneously.

In this model, the inflammatory reaction typical of inflammatory skin diseases is induced in the skin of mice (strain Balb) by allergic sensitization using a model allergen, e.g., ovalbumin (OVA) and subsequent repeated epicutaneous application over a skin patch.

The sensitization is accomplished by intraperitoneal administration (i.p.), while the treatment with DNAzyme is achieved by intradermal (i.d.) administration or epicutaneous (e.c.) administration of various formulations.

In addition to the typical histological changes in the skin, the expected increased expression of the target gene, e.g., GATA-3 and the Th2 cytokines IL-4, IL-5 and IL-13 in the inflamed area of skin is triggered and detected. By using the DNAzyme-containing formulations according to the invention as the agents for treatment of inflamed skin diseases, a therapeutic efficacy becomes apparent. Thus a significantly reduced inflammation score in mice was achieved after treating them with DNAzyme formulations. Furthermore, it was demonstrated histologically that after this treatment, pure inflammation cells in particular CD4+ T-lymphocytes could be found in the inflamed areas of skin.

For example, the following were used:

Sensitization: 10 μg OVA+10 μg Al(OH)$_3$ in 100 μL PBS, administered intraperitoneally Patches: 100 μg OVA+10 μg Al(OH)$_3$ administered cutaneously by the patch test method Treatment: 200 μg DNAzyme in 50 μL PBS applied topically intradermally and/or epicutaneously in the formulations WOW 146, WO 162 and WOW 167

The analyses have shown that the formulations containing DNAzyme are effective against experimentally-induced inflammatory skin diseases.

What is claimed:

1. A pharmaceutical composition for topical application in the form of either (i) a water-in-oil-in-water emulsion or (ii) a water-in-oil emulsion, each of said emulsions comprising a dispersed, discontinuous, internal aqueous phase, the composition comprising:

(a) at least one lipophilic emulsifier selected from the group consisting of a sorbitan fatty acid ester or a glycerol derivative;

(b) at least one consistency agent;

(c) at least one synthetic oil, natural oil, wax, or saturated hydrocarbon selected from the group consisting of paraffin or a polysiloxane;

(d) at least one additive comprising a salt or an ionic liquid, wherein the cation component of the salt or of the ionic liquid comprises an element selected from the group consisting of Na, Mg, K, Li, Ca, Fe, Cu, Ag and a combination of these elements; and, (e) at least one antisense oligonucleotide held by the internal aqueous phase, wherein the at least one antisense oligonucleotide is a DNAzyme directed against the mRNA coding for T-bet protein, the DNAzyme selected from a group consisting of DNAzymes according to SEQ ID NO 71 to SEQ ID NO 148.

2. The pharmaceutical composition according to claim 1, further comprising at least one hydrophilic emulsifier selected from the group consisting of polysorbates, ethoxylated polyethylene glycols, ethoxylated ethers, and ethoxylated esters.

3. The pharmaceutical composition according to claim 1, further comprising at least one amphiphilic component.

4. The pharmaceutical composition according to claim 3, wherein the amphiphilic component is a phospholipid.

5. The pharmaceutical composition according to claim 1, further comprising at least one humectant factor.

6. The pharmaceutical composition according to claim 5, wherein the humectant factor is selected from the group consisting of glycerol, polyols, and osmolytes.

7. The pharmaceutical composition according to claim 1, further comprising at least one preservative.

8. The pharmaceutical composition according to claim 1, wherein the lipophilic emulsifier is a sorbitan monooleate.

9. The pharmaceutical composition according to claim 1, wherein the lipophilic emulsifier is a glycerol derivative selected from the group consisting of Spans, glycerol stearate, glycerol dioleate, and glycerol monooleate.

10. The pharmaceutical composition according to claim 1, wherein the consistency agent is selected from the group consisting of a fatty acid ester, a polyethylene glycol, cera alba, a microcrystalline wax, lanolin, hydrogenated castor oil, protegin W, protegin WX, carbomers, and cellulose.

11. The pharmaceutical composition according to claim 1, wherein the synthetic oil is an esterified fatty acid or a partially esterified glyceride.

12. The pharmaceutical composition according to claim 1, wherein the natural oil is selected from the group consisting of soy oil, peanut oil, avocado oil, olive oil, castor oil, a seed oil, and a nut oil.

13. The pharmaceutical composition according to claim 1, wherein the wax is jojoba wax.

14. The pharmaceutical composition according to claim 7, wherein the preservative is paraben.

15. The pharmaceutical composition according to claim 1, wherein the cation is selected from the group consisting of Na, Mg, and a combination thereof.

16. The pharmaceutical composition according to claim 1, wherein the salt is selected from the group consisting of NaCl, $MgSO_4$, $Mg(N(SO_2CF_3)_2)_2$, and $Mg(OSO_2CF_3)_2$.

17. The pharmaceutical composition according to claim 1, wherein the ionic liquid is selected from the group consisting of 1-ethyl-3-methylimidazolium chloride, 1-butyl-3-methylimidazolium tetrafluoroborate, 1-ethyl-3-methylimidazolium sulfate, 1-ethyl-3-methylimdazolium trifluoromethane sulfonate, 1-ethyl-3-methylimidazolium dicyanamide, and 1-ethyl-1-methylpyrrolidinium bis(trifluoromethylsulfonyl) amide).

* * * * *

```
                        SEQUENCE LISTING

<160> NUMBER OF SEQ ID NOS: 148

<210> SEQ ID NO 1
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd1 DNAzyme against GATA-3mRNA

<400> SEQUENCE: 1
tcggtcagag gctagctaca acgatgcgtt gct                                    33

<210> SEQ ID NO 2
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hdg2 DNAzyme against GATA-3mRNA

<400> SEQUENCE: 2
ggcgtacgag gctagctaca acgactgctc ggt                                    33

<210> SEQ ID NO 3
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd3 DNAzyme against GATA-3mRNA

<400> SEQUENCE: 3
ggcggcgtag gctagctaca acgagacctg ctc                                    33

<210> SEQ ID NO 4
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd4 DNAzyme against GATA-3mRNA

<400> SEQUENCE: 4
ctcgggtcag gctagctaca acgactgggt agc                                    33

<210> SEQ ID NO 5
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd5 DNAzyme against GATA-3mRNA

<400> SEQUENCE: 5
```
tcctctgcag gctagctaca acgacgggt cct                                    33

<210> SEQ ID NO 6
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd6 DNAzyme against GATA-3mRNA

<400> SEQUENCE: 6
actctgcaag gctagctaca acgatctgcg agc                                    33

<210> SEQ ID NO 7
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd7 DNAzyme against GATA-3mRNA

<400> SEQUENCE: 7
gggcgacgag gctagctaca acgatctgca att                                    33

<210> SEQ ID NO 8
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd8 DNAzyme against GATA-3mRNA

<400> SEQUENCE: 8
aaggggcgag gctagctaca acgagactct gca                                    33

<210> SEQ ID NO 9
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd9 DNAzyme against GATA-3mRNA

<400> SEQUENCE: 9
aaaacgggag gctagctaca acgacaggtt gta                                    33

<210> SEQ ID NO 10
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd10 DNAzyme against GATA-3mRNA

<400> SEQUENCE: 10
agaataaaag gctagctaca acgagggacc agg                                    33

<210> SEQ ID NO 11
<211> LENGTH: 33
<212> TYPE: DNA
<213> ORGANISM: Homo sapiens
<220> FEATURE:
<221> NAME/KEY: misc_feature

```
<222> LOCATION: (1)..(33)
<223> OTHER INFORMATION: hgd11 DNAzyme against GATA-3mRNA

<400> SEQUENCE: 11
atggcagaag gctagctaca acgaaaaacg gga                                    33

<210> SEQ ID NO 12
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd12 DNAzyme against GATA-3mRNA

<400> SEQUENCE: 12
aactgggtag gctagctaca acgaggcaga ata                                    33

<210> SEQ ID NO 13
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd13 DNAzyme against GATA-3mRNA

<400> SEQUENCE: 13
atccaaaaag gctagctaca acgatgggta tgg                                    33

<210> SEQ ID NO 14
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd14 DNAzyme against GATA-3mRNA

<400> SEQUENCE: 14 agggaagag gctagctaca acgaaaaaat cca                                     33

<210> SEQ ID NO 15
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd15 DNAzyme against GATA-3mRNA

<400> SEQUENCE: 15
ttttaaaaag gctagctaca acgatatctt gga                                    33

<210> SEQ ID NO 16
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd16 DNAzyme against GATA-3mRNA

<400> SEQUENCE: 16 gtgggggag gctagctaca acgagggaag gct                                     33

<210> SEQ ID NO 17
```

```
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd17 DNAzyme against GATA-3mRNA

<400> SEQUENCE: 17
gttgaatgag gctagctaca acgattgctt tcg                          33

<210> SEQ ID NO 18
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd18 DNAzyme against GATA-3mRNA

<400> SEQUENCE: 18
gtcgttgaag gctagctaca acgagatttg ctt                          33

<210> SEQ ID NO 19
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd19 DNAzyme against GATA-3mRNA

<400> SEQUENCE: 19
ggcccggaag gctagctaca acgaccgcgc gcg                          33

<210> SEQ ID NO 20
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd20 DNAzyme against GATA-3mRNA

<400> SEQUENCE: 20
tcacctccag gctagctaca acgaggcctc ggc                          33

<210> SEQ ID NO 21
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd21 DNAzyme against GATA-3mRNA

<400> SEQUENCE: 21
ccgccgtcag gctagctaca acgactccat ggc                          33

<210> SEQ ID NO 22
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd22 DNAzyme against GATA-3mRNA

<400> SEQUENCE: 22
```

```
ggtggctcag gctagctaca acgaccagcg cgg                               33
```

<210> SEQ ID NO 23
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd23 DNAzyme against GATA-3mRNA

<400> SEQUENCE: 23

```
cgttgagcag gctagctaca acgaggcggg gtg                               33
```

<210> SEQ ID NO 24
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd24 DNAzyme against GATA-3mRNA

<400> SEQUENCE: 24

```
ccgcgtccag gctagctaca acgagtagga gtg                               33
```

<210> SEQ ID NO 25
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd25 DNAzyme against GATA-3mRNA

<400> SEQUENCE: 25

```
cagcgggtag gctagctaca acgatgcgcc gcg                               33
```

<210> SEQ ID NO 26
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd26 DNAzyme against GATA-3mRNA

<400> SEQUENCE: 26

```
gcacatccag gctagctaca acgactcctc cgg                               33
```

<210> SEQ ID NO 27
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd27 DNAzyme against GATA-3mRNA

<400> SEQUENCE: 27

```
aaaagcacag gctagctaca acgaccacct cct                               33
```

<210> SEQ ID NO 28
<211> LENGTH: 33
<212> TYPE: DNA
<213> ORGANISM: Homo sapiens
<220> FEATURE:

```
<221> NAME/KEY: misc_feature
<222> LOCATION: (1)..(33)
<223> OTHER INFORMATION: hgd28 DNAzyme against GATA-3mRNA

<400> SEQUENCE: 28
taaaaagcag gctagctaca acgaatccac ctc                                   33

<210> SEQ ID NO 29
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd29 DNAzyme against GATA-3mRNA

<400> SEQUENCE: 29
gaccgtcgag gctagctaca acgagttaaa aag                                   33

<210> SEQ ID NO 30
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd30 DNAzyme against GATA-3mRNA

<400> SEQUENCE: 30
ttgccttgag gctagctaca acgacgtcga tgt                                   33

<210> SEQ ID NO 31
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd31 DNAzyme against GATA-3mRNA

<400> SEQUENCE: 31
agggcgggag gctagctaca acgagtggtt gcc                                   33

<210> SEQ ID NO 32
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd32 DNAzyme against GATA-3mRNA

<400> SEQUENCE: 32
tggccctgag gctagctaca acgacgagtt tcc                                   33

<210> SEQ ID NO 33
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd33 DNAzyme against GATA-3mRNA

<400> SEQUENCE: 33
acctctgcag gctagctaca acgacgtggc cct                                   33
```

<210> SEQ ID NO 34
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd34 DNAzyme against GATA-3mRNA

<400> SEQUENCE: 34
cggagggtag gctagctaca acgactctgc acc                                    33

<210> SEQ ID NO 35
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd35 DNAzyme against GATA-3mRNA

<400> SEQUENCE: 35
ggcggcacag gctagctaca acgactggct ccc                                    33

<210> SEQ ID NO 36
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd36 DNAzyme against GATA-3mRNA

<400> SEQUENCE: 36
cgggcggcag gctagctaca acgaacctgg ctc                                    33

<210> SEQ ID NO 37
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd37 DNAzyme against GATA-3mRNA

<400> SEQUENCE: 37
agggatccag gctagctaca acgagaagca gag                                    33

<210> SEQ ID NO 38
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd38 DNAzyme against GATA-3mRNA

<400> SEQUENCE: 38
gggtagggag gctagctaca acgaccatga agc                                    33

<210> SEQ ID NO 39
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd39 DNAzyme against GATA-3mRNA

<400> SEQUENCE: 39
gggctgagag gctagctaca acgatccagg ggg					33

<210> SEQ ID NO 40
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd40 DNAzyme against GATA-3mRNA

<400> SEQUENCE: 40
gtggatggag gctagctaca acgagtcttg gag					33

<210> SEQ ID NO 41
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 41 DNAzyme against GATA-3mRNA

<400> SEQUENCE: 41
cgtggtggag gctagctaca acgaggacgt ctt					33

<210> SEQ ID NO 42
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 42 DNAzyme against GATA-3mRNA

<400> SEQUENCE: 42
gggggtagag gctagctaca acgaggagag ggg					33

<210> SEQ ID NO 43
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 43 DNAzyme against GATA-3mRNA

<400> SEQUENCE: 43
ggaggaggag gctagctaca acgagaggcc ggg					33

<210> SEQ ID NO 44
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd44 DNAzyme against GATA-3mRNA

<400> SEQUENCE: 44 gcccccccgag gctagctaca acgaaaggag gag					33

<210> SEQ ID NO 45
<211> LENGTH: 33
<212> TYPE: DNA
<213> ORGANISM: Homo sapiens

```
<220> FEATURE:
<221> NAME/KEY: misc_feature
<222> LOCATION: (1)..(33)
<223> OTHER INFORMATION: hgd45 DNAzyme against GATA-3mRNA

<400> SEQUENCE: 45
ccggggagag gctagctaca acgagtcctt cgg                          33

<210> SEQ ID NO 46
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd46 DNAzyme against GATA-3mRNA

<400> SEQUENCE: 46
ggacagcgag gctagctaca acgagggtcc ggg                          33

<210> SEQ ID NO 47
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd47 DNAzyme against GATA-3mRNA

<400> SEQUENCE: 47
tggggtggag gctagctaca acgaagcgat ggg                          33

<210> SEQ ID NO 48
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd48 DNAzyme against GATA-3mRNA

<400> SEQUENCE: 48
cttgaggcag gctagctaca acgatctttc tcg                          33

<210> SEQ ID NO 49
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd49 DNAzyme against GATA-3mRNA

<400> SEQUENCE: 49
cacctggtag gctagctaca acgattgagg cac                          33

<210> SEQ ID NO 50
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd50 DNAzyme against GATA-3mRNA

<400> SEQUENCE: 50 gcagggcag gctagctaca acgactggta ctt                           33
```

<210> SEQ ID NO 51
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd51 DNAzyme against GATA-3mRNA

<400> SEQUENCE: 51
ccagcttcag gctagctaca acgagctgtc ggg           33

<210> SEQ ID NO 52
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd52 DNAzyme against GATA-3mRNA

<400> SEQUENCE: 52
gtgggacgag gctagctaca acgatccagc ttc           33

<210> SEQ ID NO 53
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd53 DNAzyme against GATA-3mRNA

<400> SEQUENCE: 53
ggagtgggag gctagctaca acgagactcc agc           33

<210> SEQ ID NO 54
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd54 DNAzyme against GATA-3mRNA

<400> SEQUENCE: 54
atgctgccag gctagctaca acgagggagt ggg           33

<210> SEQ ID NO 55
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd55 DNAzyme against GATA-3mRNA

<400> SEQUENCE: 55
gggcggtcag gctagctaca acgagctgcc acg           33

<210> SEQ ID NO 56
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd56 DNAzyme against GATA-3mRNA

<400> SEQUENCE: 56
gaggctccag gctagctaca acgaccaggg cgg                                    33

<210> SEQ ID NO 57
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd57 DNAzyme against GATA-3mRNA

<400> SEQUENCE: 57
gtgggtcgag gctagctaca acgagaggag gct                                    33

<210> SEQ ID NO 58
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd58 DNAzyme against GATA-3mRNA

<400> SEQUENCE: 58
aggtggtgag gctagctaca acgaggggtg gtg                                    33

<210> SEQ ID NO 59
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd59 DNAzyme against GATA-3mRNA

<400> SEQUENCE: 59
actcgggcag gctagctaca acgagtaggg cgg                                    33

<210> SEQ ID NO 60
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd60 DNAzyme against GATA-3mRNA

<400> SEQUENCE: 60
ggagctgtag gctagctaca acgatcgggc acg                                    33

<210> SEQ ID NO 61
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd61 DNAzyme against GATA-3mRNA

<400> SEQUENCE: 61
ggacttgcag gctagctaca acgaccgaag ccg                                    33

<210> SEQ ID NO 62
<211> LENGTH: 33
<212> TYPE: DNA

```
<213> ORGANISM: Homo sapiens
<220> FEATURE:
<221> NAME/KEY: misc_feature
<222> LOCATION: (1)..(33)
<223> OTHER INFORMATION: hgd62 DNAzyme against GATA-3mRNA

<400> SEQUENCE: 62
gggcctggag gctagctaca acgattgcat ccg                              33

<210> SEQ ID NO 63
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd63 DNAzyme against GATA-3mRNA

<400> SEQUENCE: 63
tgtgctggag gctagctaca acgacgggcc ttg                              33

<210> SEQ ID NO 64
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd64 DNAzyme against GATA-3mRNA

<400> SEQUENCE: 64
gttcacacag gctagctaca acgatccctg cct                              33

<210> SEQ ID NO 65
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd65 DNAzyme against GATA-3mRNA

<400> SEQUENCE: 65
cagttcacag gctagctaca acgaactccc tgc                              33

<210> SEQ ID NO 66
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd66 DNAzyme against GATA-3mRNA

<400> SEQUENCE: 66
cacagttcag gctagctaca acgaacactc cct                              33

<210> SEQ ID NO 67
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd67 DNAzyme against GATA-3mRNA

<400> SEQUENCE: 67
gttgccccag gctagctaca acgaagttca cac                              33
```

<210> SEQ ID NO 68
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd68 DNAzyme against GATA-3mRNA

<400> SEQUENCE: 68
tcgccgccag gctagctaca acgaagtggg gtc            33

<210> SEQ ID NO 69
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd69 DNAzyme against GATA-3mRNA

<400> SEQUENCE: 69
cccgtgccag gctagctaca acgactcgcc gcc            33

<210> SEQ ID NO 70
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd70 DNAzyme against GATA-3mRNA

<400> SEQUENCE: 70
ggcgttgcag gctagctaca acgaaggtag tgt            33

<210> SEQ ID NO 71
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td1 DNAzyme against T-bet mRNA

<400> SEQUENCE: 71
tggcttctag gctagctaca acgagccctc gtc            33

<210> SEQ ID NO 72
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td2 DNAzyme against T-bet mRNA

<400> SEQUENCE: 72
gggctctgag gctagctaca acgagcctgg ctt            33

<210> SEQ ID NO 73
<211> LENGTH: 33
<212> TYPE: DNA
<213> ORGANISM: Homo sapiens
<220> FEATURE:
<221> NAME/KEY: misc_feature
<222> LOCATION: (1)..(33)

<223> OTHER INFORMATION: td3 DNAzyme against T-bet mRNA

<400> SEQUENCE: 73
gggaccccag gctagctaca acgacggagc ccg         33

<210> SEQ ID NO 74
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td4 DNAzyme against T-bet mRNA

<400> SEQUENCE: 74
ggtgggggag gctagctaca acgacccacc gga         33

<210> SEQ ID NO 75
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td5 DNAzyme against T-bet mRNA

<400> SEQUENCE: 75
ggcgggggag gctagctaca acgaccgagg gcc         33

<210> SEQ ID NO 76
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td6 DNAzyme against T-bet mRNA

<400> SEQUENCE: 76
gggctgggag gctagctaca acgagggcag gga         33

<210> SEQ ID NO 77
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td7 DNAzyme against T-bet mRNA

<400> SEQUENCE: 77
cgtcgaggag gctagctaca acgaccgccc ctc         33

<210> SEQ ID NO 78
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td8 DNAzyme against T-bet mRNA

<400> SEQUENCE: 78
gggctggcag gctagctaca acgacttccc gta         33

<210> SEQ ID NO 79
<211> LENGTH: 33

-continued

```
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td9 DNAzyme against T-bet mRNA

<400> SEQUENCE: 79
cgatgcccag gctagctaca acgaccgggg cgg                                    33

<210> SEQ ID NO 80
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td10 DNAzyme against T-bet mRNA

<400> SEQUENCE: 80
gctccacgag gctagctaca acgagcccat ccg                                    33

<210> SEQ ID NO 81
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td11 DNAzyme against T-bet mRNA

<400> SEQUENCE: 81
ccggctccag gctagctaca acgagatgcc cat                                    33

<210> SEQ ID NO 82
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td12 DNAzyme against T-bet mRNA

<400> SEQUENCE: 82
tctccgcaag gctagctaca acgaccggct cca                                    33

<210> SEQ ID NO 83
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td13 DNAzyme against T-bet mRNA

<400> SEQUENCE: 83
ccgtcagcag gctagctaca acgagtctcc gca                                    33

<210> SEQ ID NO 84
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td14 DNAzyme against T-bet mRNA

<400> SEQUENCE: 84
```
tccccggcag gctagctaca acgacggctc ggt        33

<210> SEQ ID NO 85
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td15 DNAzyme against T-bet mRNA

<400> SEQUENCE: 85
cccccgcgag gctagctaca acgagctcgt ccg        33

<210> SEQ ID NO 86
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td16 DNAzyme against T-bet mRNA

<400> SEQUENCE: 86
gtagggagag gctagctaca acgacccagg ctg        33

<210> SEQ ID NO 87
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td17 DNAzyme against T-bet mRNA

<400> SEQUENCE: 87
gggcgggcag gctagctaca acgacaaggc gcc        33

<210> SEQ ID NO 88
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td18 DNAzyme against T-bet mRNA

<400> SEQUENCE: 88
cgggaaggag gctagctaca acgatcgccc gcg        33

<210> SEQ ID NO 89
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td19 DNAzyme against T-bet mRNA

<400> SEQUENCE: 89
tagtcctcag gctagctaca acgagcggcc ccg        33

<210> SEQ ID NO 90
<211> LENGTH: 33
<212> TYPE: DNA
<213> ORGANISM: Homo sapiens
<220> FEATURE:
<221> NAME/KEY: misc_feature

```
<222> LOCATION: (1)..(33)
<223> OTHER INFORMATION: td20 DNAzyme against T-bet mRNA

<400> SEQUENCE: 90
tccccgacag gctagctaca acgactccag tcc                              33

<210> SEQ ID NO 91
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td21 DNAzyme against T-bet mRNA

<400> SEQUENCE: 91
tttccccgag gctagctaca acgaacctcc agt                              33

<210> SEQ ID NO 92
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td22 DNAzyme against T-bet mRNA

<400> SEQUENCE: 92
tgagcgcgag gctagctaca acgacctcag ttt                              33

<210> SEQ ID NO 93
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td23 DNAzyme against T-bet mRNA

<400> SEQUENCE: 93
ggaccacaag gctagctaca acgaaggtgg ttg                              33

<210> SEQ ID NO 94
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td24 DNAzyme against T-bet mRNA

<400> SEQUENCE: 94
cttggaccag gctagctaca acgaaacagg tgg                              33

<210> SEQ ID NO 95
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td25 DNAzyme against T-bet mRNA

<400> SEQUENCE: 95
aaacttggag gctagctaca acgacacaac agg                              33

<210> SEQ ID NO 96
```

```
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td26 DNAzyme against T-bet mRNA

<400> SEQUENCE: 96
ctgattaaag gctagctaca acgattggac cac                                    33

<210> SEQ ID NO 97
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td27 DNAzyme against T-bet mRNA

<400> SEQUENCE: 97
tggtgctgag gctagctaca acgataaact tgg                                    33

<210> SEQ ID NO 98
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td28 DNAzyme against T-bet mRNA

<400> SEQUENCE: 98
tgatgatcag gctagctaca acgactctgt ctg                                    33

<210> SEQ ID NO 99
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td29 DNAzyme against T-bet mRNA

<400> SEQUENCE: 99
tggtgatgag gctagctaca acgacatctc tgt                                    33

<210> SEQ ID NO 100
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td30 DNAzyme against T-bet mRNA

<400> SEQUENCE: 100
gcttggtgag gctagctaca acgagatcat ctc                                    33

<210> SEQ ID NO 101
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td31 DNAzyme against T-bet mRNA

<400> SEQUENCE: 101
```
atgggaacag gctagctaca acgaccgccg tcc                                    33

<210> SEQ ID NO 102
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td32 DNAzyme against T-bet mRNA

<400> SEQUENCE: 102
gaatgggaag gctagctaca acgaatccgc cgt                                    33

<210> SEQ ID NO 103
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td33 DNAzyme against T-bet mRNA

<400> SEQUENCE: 103
tgacaggaag gctagctaca acgagggaac atc                                    33

<210> SEQ ID NO 104
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td34 DNAzyme against T-bet mRNA

<400> SEQUENCE: 104
agtaaatgag gctagctaca acgaaggaat ggg                                    33

<210> SEQ ID NO 105
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td35 DNAzyme against T-bet mRNA

<400> SEQUENCE: 105
cacagtaaag gctagctaca acgagacagg aat                                    33

<210> SEQ ID NO 106
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td36 DNAzyme against T-bet mRNA

<400> SEQUENCE: 106
gcccggccag gctagctaca acgaagtaaa tga                                    33

<210> SEQ ID NO 107
<211> LENGTH: 33
<212> TYPE: DNA
<213> ORGANISM: Homo sapiens
<220> FEATURE:

```
<221> NAME/KEY: misc_feature
<222> LOCATION: (1)..(33)
<223> OTHER INFORMATION: td37 DNAzyme against T-bet mRNA

<400> SEQUENCE: 107
ccacaaacag gctagctaca acgacctgta gtg                                33

<210> SEQ ID NO 108
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td38 DNAzyme against T-bet mRNA

<400> SEQUENCE: 108
gtccacaaag gctagctaca acgaatcctg tag                                33

<210> SEQ ID NO 109
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td39 DNAzyme against T-bet mRNA

<400> SEQUENCE: 109
ccacgtccag gctagctaca acgaaaacat cct                                33

<210> SEQ ID NO 110
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td40 DNAzyme against T-bet mRNA

<400> SEQUENCE: 110
ccaagaccag gctagctaca acgagtccac aaa                                33

<210> SEQ ID NO 111
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td41 DNAzyme against T-bet mRNA

<400> SEQUENCE: 111
ccaccaagag gctagctaca acgacacgtc cac                                33

<210> SEQ ID NO 112
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td42 DNAzyme against T-bet mRNA

<400> SEQUENCE: 112
gctggtccag gctagctaca acgacaagac cac                                33
```

<210> SEQ ID NO 113
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td43 DNAzyme against T-bet mRNA

<400> SEQUENCE: 113
gctctggtag gctagctaca acgacgccag tgg              33

<210> SEQ ID NO 114
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td44 DNAzyme against T-bet mRNA

<400> SEQUENCE: 114
ctgcacccag gctagctaca acgattgccg ctc              33

<210> SEQ ID NO 115
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td45 DNAzyme against T-bet mRNA

<400> SEQUENCE: 115
cacactgcag gctagctaca acgaccactt gcc              33

<210> SEQ ID NO 116
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td46 DNAzyme against T-bet mRNA

<400> SEQUENCE: 116
ctttccacag gctagctaca acgatgcacc cac              33

<210> SEQ ID NO 117
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td47 DNAzyme against T-bet mRNA

<400> SEQUENCE: 117
gcctttccag gctagctaca acgaactgca ccc              33

<210> SEQ ID NO 118
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td48 DNAzyme against T-bet mRNA

<400> SEQUENCE: 118
ttcctggcag gctagctaca acgagctgcc ctc     33

<210> SEQ ID NO 119
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td49 DNAzyme against T-bet mRNA

<400> SEQUENCE: 119
gtggacgtag gctagctaca acgaaggcgg ttt     33

<210> SEQ ID NO 120
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td50 DNAzyme against T-bet mRNA

<400> SEQUENCE: 120
ccgggtggag gctagctaca acgagtacag gcg     33

<210> SEQ ID NO 121
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td51 DNAzyme against T-bet mRNA

<400> SEQUENCE: 121
cctggcgcag gctagctaca acgaccagtg cgc     33

<210> SEQ ID NO 122
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td52 DNAzyme against T-bet mRNA

<400> SEQUENCE: 122
caaatgaaag gctagctaca acgattcctg gcg     33

<210> SEQ ID NO 123
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td53 DNAzyme against T-bet mRNA

<400> SEQUENCE: 123
tttcccaaag gctagctaca acgagaaact tcc     33

<210> SEQ ID NO 124
<211> LENGTH: 33
<212> TYPE: DNA
<213> ORGANISM: Homo sapiens

```
<220> FEATURE:
<221> NAME/KEY: misc_feature
<222> LOCATION: (1)..(33)
<223> OTHER INFORMATION: td54 DNAzyme against T-bet mRNA

<400> SEQUENCE: 124
attgttggag gctagctaca acgagccccc ttg                                    33

<210> SEQ ID NO 125
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td55 DNAzyme against T-bet mRNA

<400> SEQUENCE: 125
tgggtcacag gctagctaca acgatgttgg acg                                    33

<210> SEQ ID NO 126
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td56 DNAzyme against T-bet mRNA

<400> SEQUENCE: 126
tctgggtcag gctagctaca acgaattgtt gga                                    33

<210> SEQ ID NO 127
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td57 DNAzyme against T-bet mRNA

<400> SEQUENCE: 127
gcacaatcag gctagctaca acgactgggt cac                                    33

<210> SEQ ID NO 128
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td58 DNAzyme against T-bet mRNA

<400> SEQUENCE: 128
ggagcacaag gctagctaca acgacatctg ggt                                    33

<210> SEQ ID NO 129
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td59 DNAzyme against T-bet mRNA

<400> SEQUENCE: 129
actggagcag gctagctaca acgaaatcat ctg                                    33
```

```
<210> SEQ ID NO 130
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td60 DNAzyme against T-bet mRNA

<400> SEQUENCE: 130
atggagggag gctagctaca acgatggagc aca                                   33

<210> SEQ ID NO 131
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td61 DNAzyme against T-bet mRNA

<400> SEQUENCE: 131
tggtacttag gctagctaca acgaggaggg act                                   33

<210> SEQ ID NO 132
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td62 DNAzyme against T-bet mRNA

<400> SEQUENCE: 132
gggctggtag gctagctaca acgattatgg agg                                   33

<210> SEQ ID NO 133
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td63 DNAzyme against T-bet mRNA

<400> SEQUENCE: 133
tcaacgatag gctagctaca acgagcagcc ggg                                   33

<210> SEQ ID NO 134
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td64 DNAzyme against T-bet mRNA

<400> SEQUENCE: 134
cctcaacgag gctagctaca acgaatgcag ccg                                   33

<210> SEQ ID NO 135
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td65 DNAzyme against T-bet mRNA
```

```
<400> SEQUENCE: 135
tcacctcaag gctagctaca acgagatatg cag                                33

<210> SEQ ID NO 136
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td66 DNAzyme against T-bet mRNA

<400> SEQUENCE: 136
cgtcgttcag gctagctaca acgactcaac gat                                33

<210> SEQ ID NO 137
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td67 DNAzyme against T-bet mRNA

<400> SEQUENCE: 137
gtaaagatag gctagctaca acgagcgtgt tgg                                33

<210> SEQ ID NO 138
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td68 DNAzyme against T-bet mRNA

<400> SEQUENCE: 138
aagtaaagag gctagctaca acgaatgcgt gtt                                33

<210> SEQ ID NO 139
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td69 DNAzyme against T-bet mRNA

<400> SEQUENCE: 139
ggcaatgaag gctagctaca acgatgggtt tct                                33

<210> SEQ ID NO 140
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td70 DNAzyme against T-bet mRNA

<400> SEQUENCE: 140
tcacggcaag gctagctaca acgagaactg ggt                                33

<210> SEQ ID NO 141
<211> LENGTH: 33
<212> TYPE: DNA
```

<213> ORGANISM: Homo sapiens
<220> FEATURE:
<221> NAME/KEY: misc_feature
<222> LOCATION: (1)..(33)
<223> OTHER INFORMATION: td71 DNAzyme against T-bet mRNA

<400> SEQUENCE: 141
aggcagtcag gctagctaca acgaggcaat gaa         33

<210> SEQ ID NO 142
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td72 DNAzyme against T-bet mRNA

<400> SEQUENCE: 142
atctcggcag gctagctaca acgatctggt agg         33

<210> SEQ ID NO 143
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td73 DNAzyme against T-bet mRNA

<400> SEQUENCE: 143
gctgagtaag gctagctaca acgactcggc att         33

<210> SEQ ID NO 144
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td74 DNAzyme against T-bet mRNA

<400> SEQUENCE: 144
tattatcaag gctagctaca acgatttcag ctg         33

<210> SEQ ID NO 145
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td75 DNAzyme against T-bet mRNA

<400> SEQUENCE: 145
gggttattag gctagctaca acgacaattt tca         33

<210> SEQ ID NO 146
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td76 DNAzyme against T-bet mRNA

<400> SEQUENCE: 146
aaggggttag gctagctaca acgatatcaa ttt         33

-continued

```
<210> SEQ ID NO 147
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td77 DNAzyme against T-bet mRNA

<400> SEQUENCE: 147
ctcccggaag gctagctaca acgacctttg gca                          33

<210> SEQ ID NO 148
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td78 DNAzyme against T-bet mRNA

<400> SEQUENCE: 148
gtacatggag gctagctaca acgatcaaag ttc                          33
```